United States Patent [19]

Trasen

[11] Patent Number: 4,810,388
[45] Date of Patent: Mar. 7, 1989

[54] PORTABLE INTRAVENOUS SOLUTIONS AND WATER FOR INJECTION APPARATUS AND METHOD

[76] Inventor: Ben Trasen, 7275 S. Jackson Ct., Littleton, Colo. 80122

[21] Appl. No.: 93,696

[22] Filed: Sep. 8, 1987

[51] Int. Cl.$^4$ .................. B01D 13/00; B01D 15/04
[52] U.S. Cl. ..................... 210/638; 210/655; 210/669; 210/96.2; 210/238; 210/257.2; 210/416.3
[58] Field of Search ............ 210/638, 655, 663, 669, 210/96.2, 195.2, 202, 203, 237, 238, 244, 257.2, 416.3, 900

[56] References Cited

U.S. PATENT DOCUMENTS

| | | |
|---|---|---|
| 2,325,169 | 7/1943 | Alsop . |
| 2,566,371 | 9/1951 | Quinn ................... 210/416.3 |
| 2,649,205 | 8/1953 | Quinn ................... 210/416.3 |
| 3,327,859 | 6/1967 | Pall ....................... 210/266 |
| 3,542,199 | 11/1970 | Bray et al. ............. 210/257.2 X |
| 3,950,253 | 4/1976 | Stern ..................... 210/416.3 X |
| 4,049,550 | 9/1977 | Obidniak ............... 210/244 |
| 4,110,219 | 8/1978 | Maples .................. 210/257.2 X |
| 4,160,727 | 7/1979 | Harris, Jr. ............. 210/900 X |
| 4,218,317 | 8/1980 | Kirschmann .......... 210/416.3 |
| 4,269,708 | 5/1981 | Bonomini et al. ..... 210/257.2 X |
| 4,277,332 | 7/1981 | Baughn ................. 210/96.2 |
| 4,277,333 | 7/1981 | Coppola ................ 210/136 |
| 4,280,912 | 7/1981 | Berry, III et al. ..... 210/900 X |
| 4,430,226 | 2/1984 | Hegde et al. .......... 210/900 X |
| 4,477,347 | 10/1984 | Sylva .................... 210/232 |
| 4,495,067 | 1/1985 | Klein et al. ........... 210/257.2 X |
| 4,528,093 | 7/1985 | Winer ................... 210/416.3 X |
| 4,534,713 | 8/1985 | Wanner ................. 210/416.3 X |
| 4,548,716 | 10/1985 | Boeve ................... 210/900 X |
| 4,595,498 | 6/1986 | Cohen et al. .......... 210/257.2 X |
| 4,609,466 | 9/1986 | McCausland et al. . 210/257.2 X |
| 4,622,133 | 11/1986 | Furuno .................. 210/900 X |
| 4,623,467 | 11/1986 | Hamlin .................. 210/257.2 X |
| 4,626,346 | 12/1986 | Hall ....................... 210/257.2 X |
| 4,650,586 | 3/1987 | Ellis, III ................ 210/257.2 X |
| 4,684,460 | 8/1987 | Issautier ................ 210/257.2 X |

FOREIGN PATENT DOCUMENTS

1436111  5/1976  United Kingdom ............ 210/257.2

*Primary Examiner*—Robert Spitzer
*Attorney, Agent, or Firm*—J. Nevin Shaffer, Jr.

[57] ABSTRACT

A portable assembly of components that is designed to produce sterile, intravenous solutions and water for injection in the field, under combat conditions and from various sources of raw feedwater. A single frame supports the components of the invention consisting of a pair of manually operated pump handles, a peristaltic pump to which is engaged an inlet feed tube. The device has the ability to suck water from available feedwater sources or from a reserve bottle designed to hold a variety of liquids that may be introduced therein from any available source. Feedwater is pumped into the base of a filter module containing a coarse filter combined with a reserve osmosis filter for an initial prefiltering of the water. Purified water then passes through a carbon exchange column and subsequently an ion exchange column. At this point, ultrapure water is then passed through a sterilizing filter from which it passes through an IV spike in the form of sterile, non-pyrogenic water for injection. Prepackaged, large volume parenteral bags with premeasured dried medicines located inside are provided so that when connected to the IV spike, IV solutions can be created from the reconstituted medicines. The invention is portable, disposable, air dropable, and can produced 20 to 40 liters of sterile, non-pyrogenic intravenous solutions and water for injection prior to shut down by depletion of the filter system.

26 Claims, 5 Drawing Sheets

PORTABLE INTRAVENOUS SOLUTIONS AND WATER FOR INJECTION APPARATUS AND METHOD

BACKGROUND OF THE INVENTION

This invention relates to a unique apparatus and method of providing sterile, non-pyrogenic intravenous solutions and water for injection.

Both manual and automatically driven filters have been known in the art for quite some time. For example, automatically powered filter and pump combinations have been designed to be part of a movable platform upon which the filter is positioned with the electric motor underneath the filter shielded from spray by a cover. Such a device is disclosed in Alsop, U.S. Pat. No. 2,325,169 which utilizes removable pads for gross filtering of fluids, primarily used in connection with plating baths. A variety of non-electric water filters have been previously disclosed. For instance, Quinn, U.S. Pat. No. 2,566,371 discloses a portable drinking water filter system usable for military operations. The device has a lens built into the top of the system whereby a visual examination of the water before and after filtering is made possible. Pall, U.S. Pat. No. 3,327,859 discloses a portable filter which is powered by the user sucking water through the filtering device. Additionally, the Coppla device, U.S. Pat. No. 4,277,333, discloses a portable filter system for back packers which allegedly weighs less than a pound and is manually operated by a hand pump. Also, Sylva, U.S. Pat. No. 4,477,347, discloses a small cup sized, portable, hand pumped, filter system designed to provide up to one liter of clean drinkable water before the filter clogs.

The purpose of all these prior art devices was to provide drinking water. None of the electrically powered and manually operated filter systems known in the art, however, can produce injectable sterile non-pyrogenic water for injection. Further, none of the prior art devices are capable of producing significant amounts of fluid, injectable or otherwise. Thus, there is a need in the art for providing a portable intravenous solution device which can produce sterile, non-pyrogenic intravenous solutions and water for injection either for introduction into prepositioned dry intravenous bags containing dried drugs which are reconstituted by the introduction of this sterile liquid or for use directly for irrigation of wounds on site. It, therefore, is an object of this invention to provide an improved portable intravenous solutions and water for injection apparatus and method for the provision of large quantities of sterile, non-pyrogenic water for injection and intravenous solutions.

SHORT STATEMENT OF THE INVENTION

Accordingly, the portable intravenous solution mechanism of the present invention includes a central structural frame, across the top of which is a handle for carrying. A rigid lightweight plastic outer box is attached to the structural frame. This outer box encloses all the components of the invention. Additionally, the outer plastic box has a detachable corner which allows easy access to the area of the invention where the collapsed IV bags are filled during operation. Further, there are collapsible handles attached on opposite sides of the box frame which are connected to a shaft that runs through a pump which is located and attached to the central structural frame inside of the hollow box. The pump is a manually operated peristaltic or roller pump which rhythmically compresses a portion of a tube against the inside of the housing of the pump. One end of the tube is the inlet end from which a suction is drawn on the water to be treated. The tube then passes around the pump, as previously described, and has an exit end which is connected to the inlet port of a prefilter/reverse osmosis filter. The ability to attach an extension to the inlet tube is provided with the device so that a remote water source that may be some distance from the device, may be utilized. In the event that there is no nearby water source the device has a self-contained reservoir tank within the box designed to hold a quantity of water or similar liquid which has been poured therein. When this reservoir is utilized, the inlet end of the pumping tube is attached to an outlet port on the reservoir tank so that suction is taken on the reservoir and liquid is pumped into the filter system.

Initial treatment of contaminated water is conducted by a combination prefilter and reverse osmosis module both of which are located in a single sealed container. In the initial stage, the prefilter removes coarse contaminants such as mud, sand, leaves, etc. and passes the initially filtered liquid to the reverse osmosis (RO) module. The reverse osmosis module operates in a known manner and passes contaminated liquid to a drain and purified water to the exit port of the prefilter/reverse osmosis module. The device contains a valve in the drain line which is designed to function as a variable restricting orifice and increases the pressure within the RO module which enables it to separate pure water from contaminated water. The contaminated water exits through a drain. The valve incorporates stops permitting three to four orifice settings. Using a more restrictive setting increases the amount of pure water produced. However, since this also decreases the amount of contaminated water and raises its concentration, fouling of the membranes of the device can occur. Thus, when the quality of the feed stream is high, that is not very contaminated, the valve is restricted to a minimum and more purified water is produced. On the other hand, when feed stream quality is poor, the valve is opened to a larger orifice setting to reduce fouling.

Upon exiting the reverse osmosis module, purified water enters a carbon column wherein organic molecules and halogens are removed and the purified water then passes to an ion exchange column which removes ionizable substances thereby producing "ultrapure" water. Both the carbon and ion exchange columns incorporate an internal trap filter at their outlet ends to prevent migration of small particles and resin beads from going downstream.

A unique final filtering stage consists of a sterilizing filter which receives the ultrapure water and removes all microorganisms, pyrogens and any remaining organics so that sterile, non-pyrogenic water for injection is produced. The final filter is a presterilized capsule-type unit having a pleated microfilter element rated at 0.2 um or smaller and sealed within a plastic housing in a unitary design. The filter medium has an electrical charge which enables it to remove pyrogens and trace organics.

Ultimately, this sterile, non-pyrogenic water for injection is passed through an intravenous spike designed to be inserted into the previously described dry, prepckaged intravenous bags containing measured amounts of medicines for use in the field as IV solutions. Also, as already mentioned, the device is useful for the production of sterile, non-pyrogenic water for injection that may be applied directly to wounds for irrigation thereof due to the fact that the device can produce large quantities of such sterile, non-pyrogenic water.

Even under the severest conditions, such as where the supply of water is from polluted, muddy puddles, volumes greater than 20 liters can be produced. With a supply from lake, stream or other similar sources, a volume greater than 40 liters can be produced before the purification components are depleted. Compared to existing devices, this tremendous increase in available volume enables the adequate treatment of many more wounded or injured individuals. The invention weighs approximately 19 pounds (8.6 kg) dry. The weight of six large volume parenteral (LVP) bags full of solution is just over 13 pounds (6.0 kg). Further, the invention is designed and packaged such that it is "air dropable". Additionally, the device is a one-time use disposable kit. Fully packed, it contains twenty IV administrative sets, twenty empty one liter bags and two full LVP bags. The IV administrative sets contain approximately three feet of ⅛" plastic tubing which is connected at one end to the IV bag and the other end of which connects to a needle or catheter and is inserted intravenously. The "empty" bags contain powdered or dried pharmaceutical for reconstitution.

The device is not washed and cleaned and/or reused. All components are dry and cannot deteriorate or become affected by long-term storage. It is expected, therefore, that the kit can lie dormant for periods of over ten years and then be fully functional upon demand.

Currently, LVP solutions have expiration dates beyond which they should not be used. Sterile liquids stored in plastic bags under varying environmental conditions can undergo many changes that can render them unsafe for use. Such changes include leakage, extractables from the plastic dissolving in the solution, and interaction of the drug due to high temperatures or varying temperatures over time. Freezing of solutions may also be harmful over time. Additionally, leakage or a minor porosity, not showing a detectable leak, could result in the loss of sterility.

The device of this invention avoids these prior art problems. Other advantages of this invention are that all purification components are modular and there are no moving parts that come into contact with the pumped fluid. Additionally, three components incorporate integral filters, thus reducing the number of connections necessary in the device. Further, the device can convert into sterile water for injection, water obtained from most natural sources including: streams, lakes, puddles, mines, wells, muddy water, biologically-contaminated water, sewerage, and urine.

Still further, there is no requirement for an outside source of power or batteries that either would need replacement or be dead after long periods of storage. This invention is operated without electricity at all and thus has no wires or generators as well. Because it is not electrically driven, it produces no radio frequencies, heat or infra-red rays, which could possibly be detected, thereby disclosing the presence of the individuals using the device.

Importantly, the components of the invention are unaffected by either chlorine or iodine that may have been added to canteen water. Further, both chlorine and iodine are removed by the invention. Additionally, it is known that LVP solutions freeze easily in subfreezing temperatures. Once frozen, they are difficult to thaw and too cold to administer after thawing. Solutions prepared by the invention, however, would not be frozen because no liquid is stored. Finally, the invention produces large volumes of sterile water, much of which could be used directly, without collection in LVP bags, for irrigation of wounds.

BRIEF DESCRIPTION OF THE DRAWINGS

Other objects, features and advantages of the present invention will become more fully apparent from the following detailed description of the preferred embodiment, the appended claims and the accompanying drawings in which:

DETAILED DESCRIPTION OF THE PREFERRED EMBODIMENT

The preferred embodiment of the present invention is illustrated by way of example in FIGS. 1-13. With specific reference to FIGS. 1 and 2, the portable intravenous solutions and water for injection device 10 includes a frame 12 and carrying handle 14. Frame 12 is a rigid rectangular center piece measuring 10½" wide by 21¼" high by ¾" thick. It is the backbone of device 10 to which all the components are attached.

Figure 2:
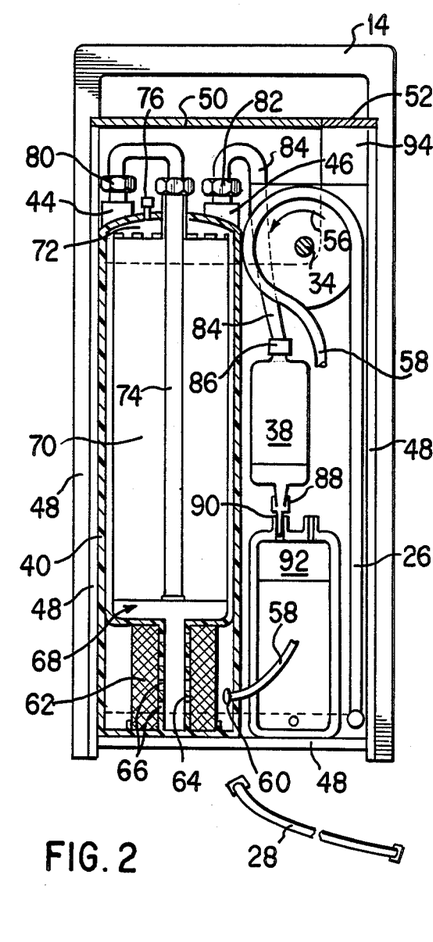
FIG. 2 is a left side view with removable panels removed and an additional section of the left side deleted so that the interior of the device can be seen.
Figure 3:
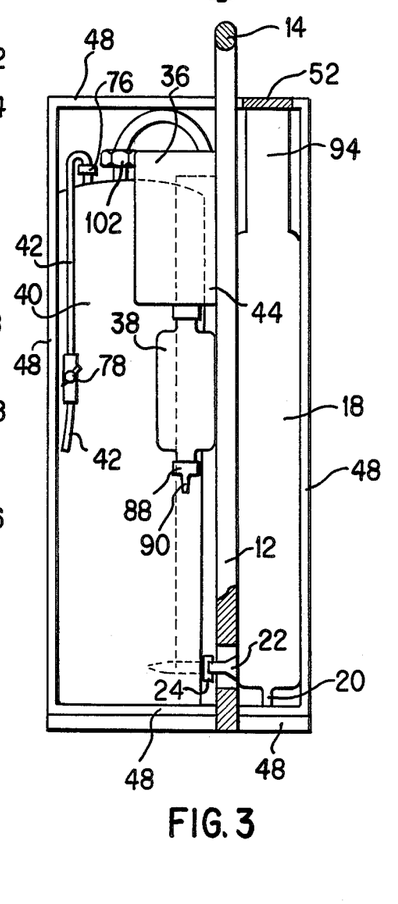
FIG. 3 is a front view of the invention with the removable panel removed and the remainder of the side of the device deleted so that the interior of the device may be seen.

The front 16 of device 10 is the side facing the operator during operation. The right side of frame 12 contains a plastic reservoir tank 18 which measures 15" high by 9" wide by 2" deep and has the capacity of 4.4 liters. Reservoir 18 stands off from the bottom of frame 12 by means of a plastic rim 20 (as shown in FIG. 3) in order to allow complete drainage of reservoir 18. As also sown in FIG. 3, tank 18 has an outlet 22 that protrudes through frame 12 near the bottom and has a fitting 24 to which a pump inlet tube 26 can be attached (pump inlet tube 26 is shown in FIG. 2). Alternatively, a feedwater hose 28 can be connected to pump inlet tube 26 so that water from a remote source may be obtained.

Figure 1:
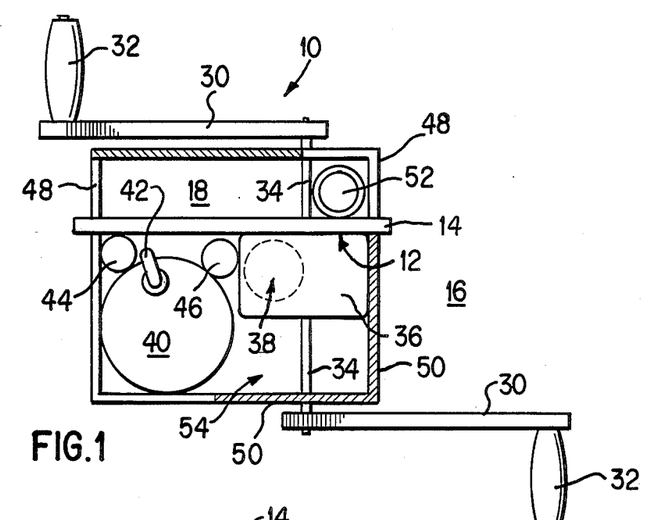
FIG. 1 is a top view of a preferred embodiment of the portable intravenous solution mechanism of the present invention with the pump cranking handles in the unfolded position.

FIG. 1 further illustrates two oppositely positioned cranking arms 30 to which are attached identical cranking handles 32. Cranking arms 30 are connected to pump crank shaft 34 which passes through peristaltic pump 36 which is, in turn, held in position on frame 12.

FIG. 1 also shows, in dotted lines, sterilizing filter 38, prefilter and reverse osmosis module 40, drain tube 42, carbon column 44 and ion exchange column 46. Additionally, a rigid lightweight plastic outer box 48 and removable side (FIG. 1) and top (FIG. 2) panels 50, location, when in place, shown in cross-hatches, are illustrated.

Finally, FIG. 1 illustrates removable reservoir screw-type fill cap 52 and inner chamber 54. Inner chamber 54 measures approximately 5½" wide by 4" deep by 13½" high. When device 10 is packed for storage (See FIGS. 11-13), inner chamber 54 contains a minimum of twenty collapsed, empty, large volume parenteral (LVP) bags 108 and twenty IV administration sets 110. It also contains two full, ready-to-use LVP bags 112.

Turning to FIG. 2, arrow 56 indicates the direction of rotation of peristaltic pump 36 and illustrates clearly that pump inlet tube 26 passes inside peristaltic pump 36. Having passed through peristaltic pump 36, pump inlet tube 26 becomes pump outlet tube 58 which, in turn, is connected by connection 60 to the inlet at the bottom of prefilter and reverse osmosis module 40. Prefilter and reverse osmosis module 40 is a plastic cylindrical chamber measuring 4¾" in diameter by 17½" long. At the inlet end near connection 60 is a 4" long by 2¾" diameter coarse filter spool 62 fitted to a central core 64. Central core 64 has small openings 66 to permit the flow of water to an upstream chamber 68 of a reverse osmosis element 70. Water leaving the reverse osmosis element 70 flows either into a downstream chamber 72 if it is reject water, or up through center core 74 if it is pure water. Rejected water exits downstream chamber 72 through fitting 76.

FIG. 3 illustrates that after passing through fitting 76, reject water goes through discharge valve 78 (See also FIG. 5) and then drains from the device through drain tube 42.

Figure 4:
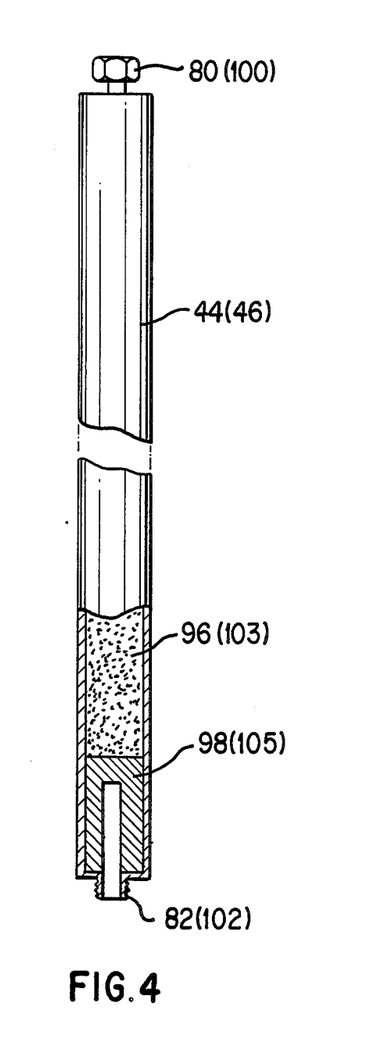
FIG. 4 is a side view of a representation of the carbon column and ion exchange column shown in partial cutaway so that the interior of the columns may be seen.

Referring to FIG. 2 again, pure water flows from the center core 74 to inlet fitting 80 of carbon column 44 (See also FIG. 4). Carbon column 44 has a 1" inside diameter by 16¼" length. Pure water flow exits at outlet 82 (not shown) through the bottom of carbon column 44 and flows to the inlet connection 100 (not shown) at the bottom of ion exchange column 46. Ion exchange column 46 has a 1" inside diameter by 16¼" long length. Pure water exits the ion exchange column 46 through outlet fitting 102. Fitting 102 is connected to transfer tube 84 that connects to the inlet 86 of sterilizing filter 38. The outlet 88 of sterilizing filter 38 is connected to an intravenous (IV) spike 90. Collapsed LVP bag 92 is placed in position beneath and connected to, sterilizing filter 38 and filled by means of IV spike 90.

FIGS. 2 and 3 both illustrate fill neck 94 of plastic reservoir tank 18.

Turning now to FIG. 4, carbon column 44 is more fully illustrated. Carbon column 44 is filled with activated carbon 96 and has a trap filter 98 located just in front of carbon column outlet 82. Ion exchange column 46 is of substantially identical construction and its individual parts are identified in parenthesis, with inlet 100 and outlet 102 demonstrating the direction of flow of material through this device. Also, ion exchange column 46 is filled with ion exchange resin 103 in place of carbon 96.

Figure 5:
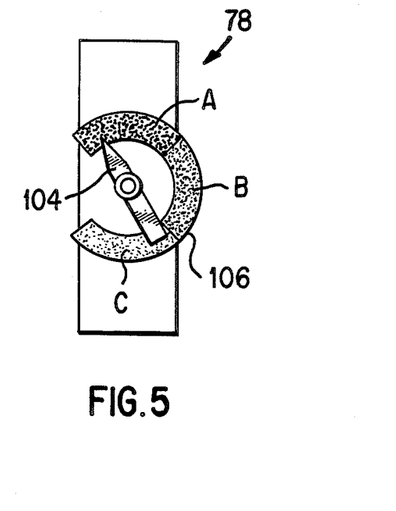
FIG. 5 is a detailed view of the restriction valve of the invention.
Figures 6, 7:
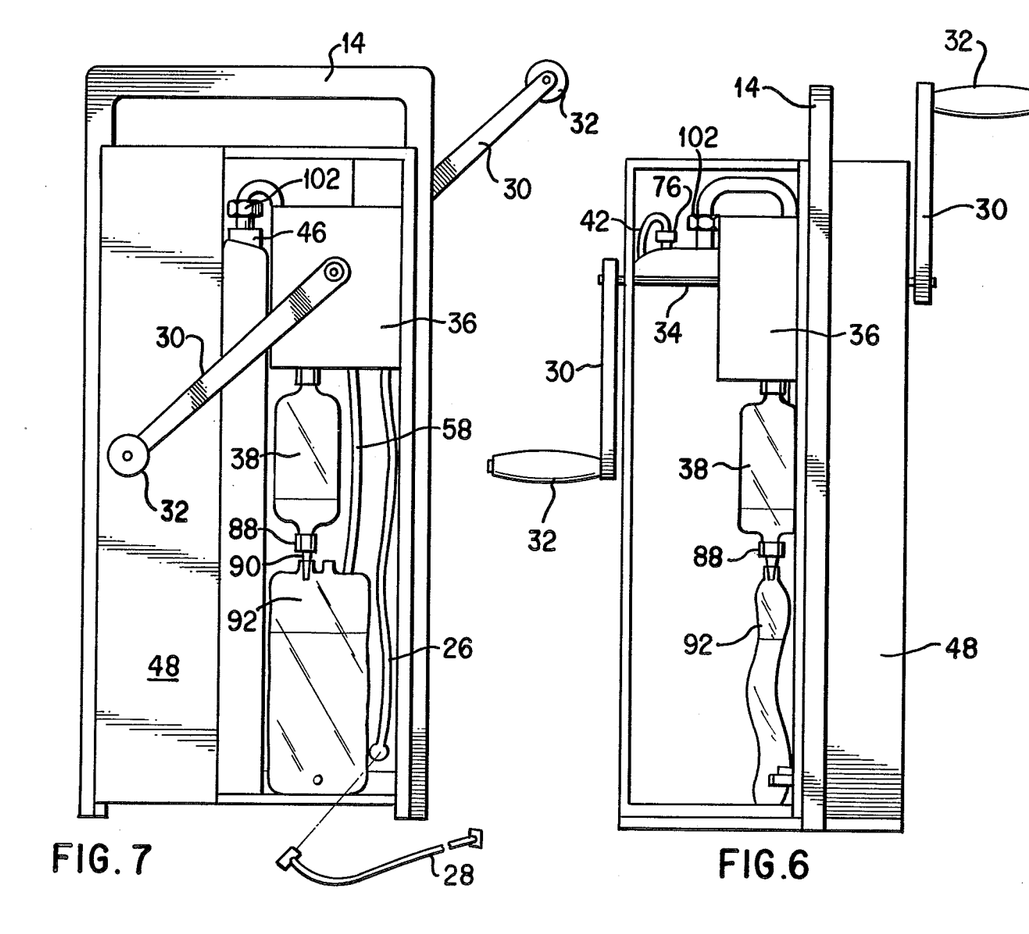
FIG. 6 is a front view, with cover panels removed, unpacked and ready for operation.
FIG. 7 is a side view, with cover panels removed, unpacked and ready for operation.
Figure 8:
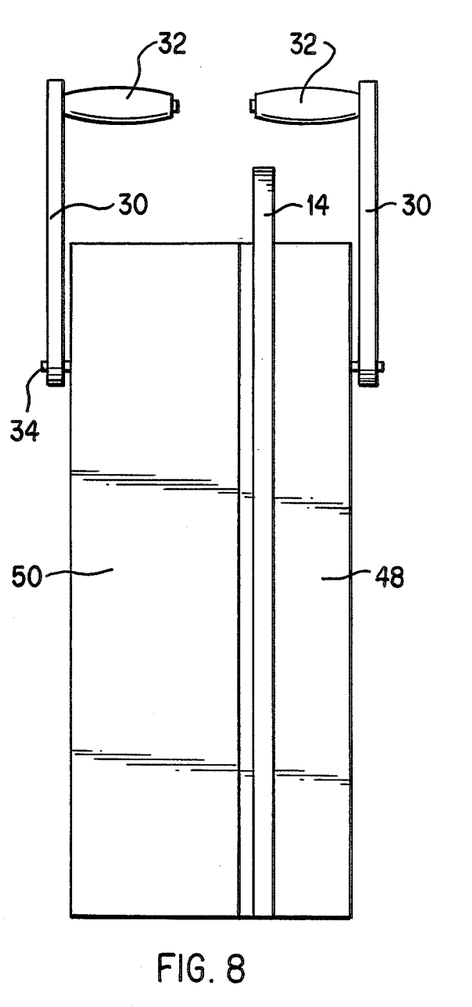
FIG. 8 is a front view with handles in "collapsed" position for storage and with carrying cover panels in place.
Figure 9:
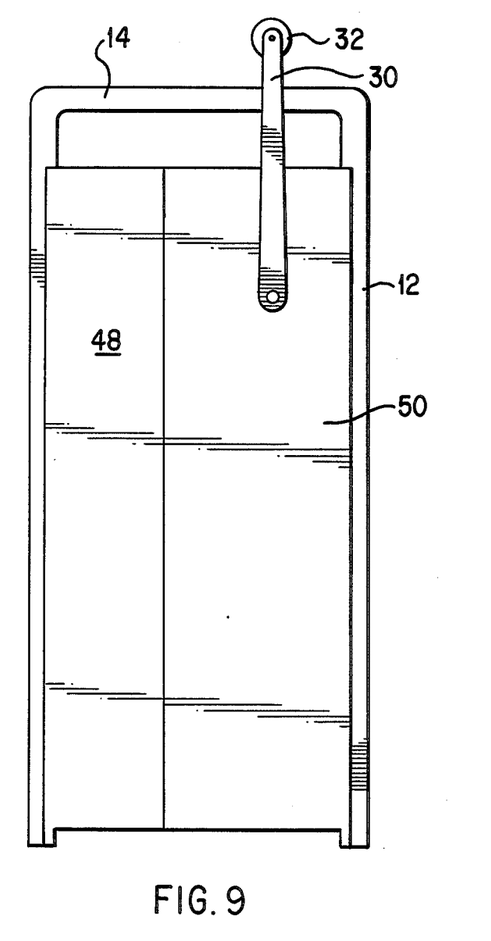
FIG. 9 is a side view of FIG. 8.
Figure 10:
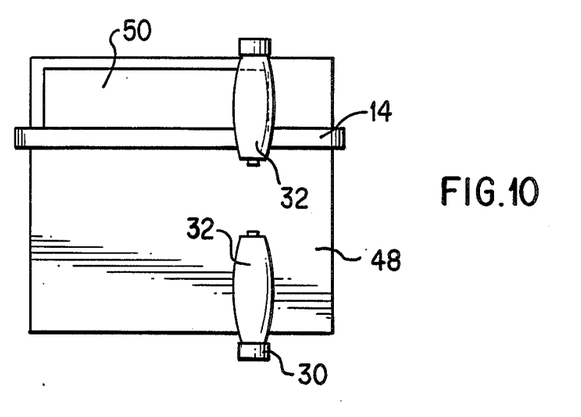
FIG. 10 is a top view of FIG. 9.
Figures 11, 12:
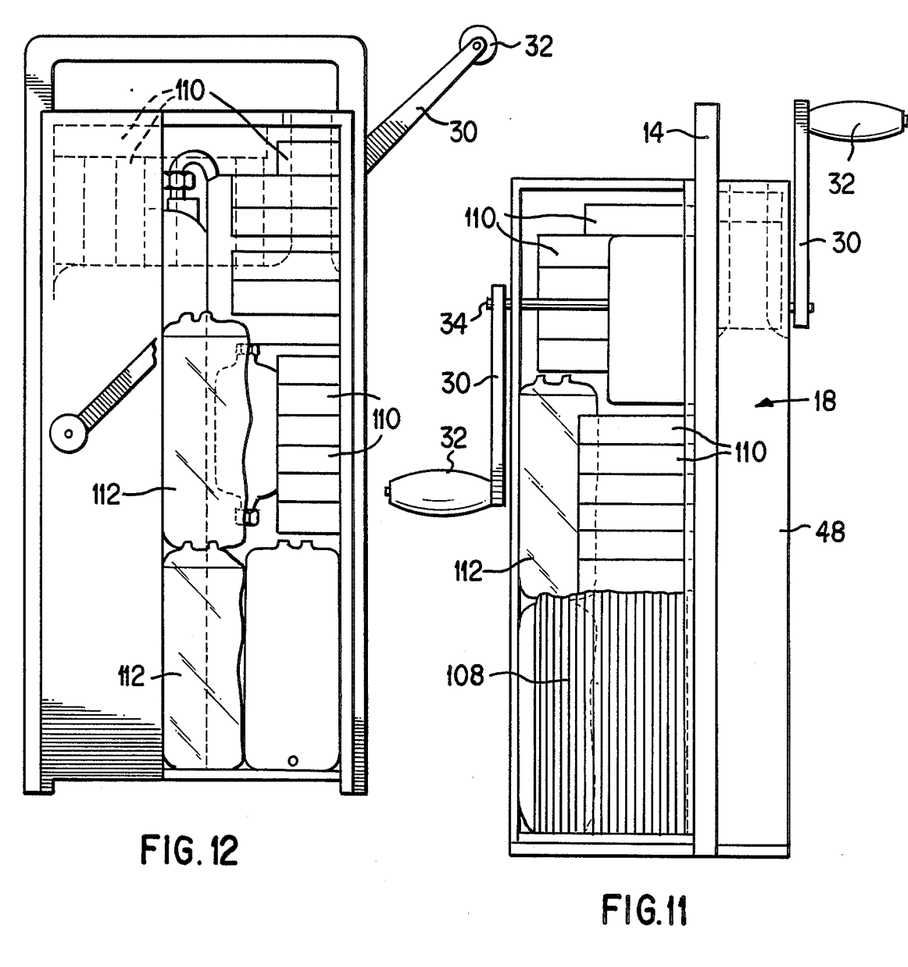
FIG. 11 is a front view, with covers removed, fully packed with twenty empty IV bags, twenty IV sets and two full IV bags.
FIG. 12 is a side view of FIG. 11.
Figure 13:
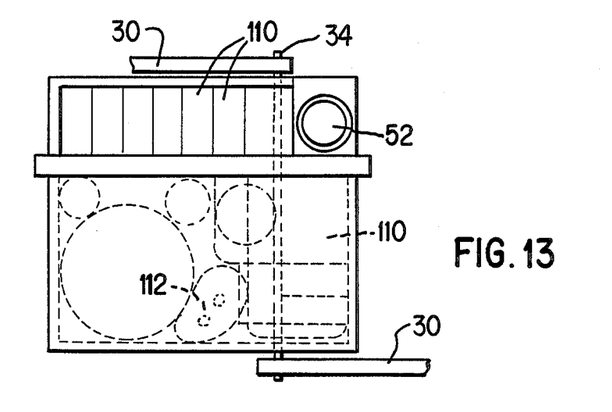
FIG. 13 is a top view of FIG. 12.

Referring now to FIG. 5, discharge valve 78 is illustrated with the flow direction from the top of the drawing towards the bottom of the drawing. Valve pointer handle 104 and contamination scale 106 are illustrated. The darker gradients on contamination scale 106 indicate very dirty water position "A", the midrange hash markings indicate dirty water positions "B", and the large cross hatchings indicate clear water positions "C". As previously discussed, with pointer handle 104 in the very dirty feedwater position "A", large amounts of contaminated water are allowed to exit from device 10. The cleaner the feedwater, the more raw water may be passed through device 10 and the more pure water may be produced without fouling device 10. In this case, pointer handle 104 may be moved farther and farther towards a more restricted, clean water, position "C".

In operation, portable intravenous solution device 10 is set down on the ground on its base with carrying handle 14 on top and the device in a vertical position. If a supply of natural feedwater is nearby, feedwater hose 28 is connected to pump inlet tube 26, then uncoiled and the upstream end is immersed in the available feedwater. If natural feedwater is not present, the feedwater hose 28 is not used. In this instance, pump inlet tube 26 is connected to fitting 24 of plastic reservoir tank 18. Water obtained from drinking canteens, other water supplies used by the unit, or even urine is poured into reservoir tank 18 through fill neck 94.

Removable panels 50 are removed and discarded. This exposes the inner chamber 54 which contains sterilizing filter 38, the supply of twenty LVP IV bags 108, twenty administration sets 110 and two full, commercially-prepared, LVP bags 112. These prepared solutions 112 are furnished for the purpose of administering immediately to wounded while additional bags of IV solution are being generated.

Next, the collapsed bags 108, administration sets 110 and full LVP bags 112 are removed from the inner chamber 54 leaving a space measuring approximately 4" deep by 5½" wide by 13½" high in which to prepare the solutions. A cap (not shown) is then removed from the inlet fitting 86 of sterilizing filter 38 and connection is made. A cap (not shown) is then removed from the outlet IV spike 90 on the sterilizing filter 38 and a collapsed sterile LVP bag 92 (108) containing only powdered or dried pharmaceutical, is carefully, aseptically connected to the IV spike 90; the cap (not shown) being removed from the inlet port of the bag 92 and the spike 90 being quickly inserted into the port. The bag 92 will then stand up in the inner chamber 54 as shown in FIG. 2.

An operator then sits on the ground with the portable intravenous solution device 10 between his legs and the front 16 and the open inner chamber 54 containing the sterilizing filter 38 and LVP bag 92 facing him. Cranking arms 30 and crank handles 32 are assembled. Crank arms are fastened to the pump shaft 34 by means of a spline (not shown). For operation, a cotter pin (not shown) is first removed, the crank arms are slipped off the shaft 34, reversed and the cotter pins returned to their former positions. Crank arms 30 are opposed by 180 degrees. Portable intravenous solution device 10 is now ready for operation. The user then turns crank arms 30 in the normal direction, that is, by pushing away from the body at the top of the rotation in the direction of direction arrow 56. A rachet wheel (not shown) located on the peristaltic pump 36 prevents reverse rotation.

By rapidly cranking the manual pump 36, feedwater is drawn in, either from the feedwater supply or from the reservoir tank 18, and pumped to the inlet 60 of prefilter and reverse osmosis module 40. From this module 40, pure water is pumped first to the carbon column 44 and then to the ion exchange column 46. It then goes to inlet 86 of the sterilizing, and depyrogenating, filter 38. Here, the final stages of purification are performed and pure, sterile intravenous solutions and water for injection are generated. The water for injection emerges through IV spike 90 and into the collapsed LVP bag 92 where it reconstitutes the dried drug, previously mentioned. When approximately one litre has been collected, the bag 92 is removed and capped and the next collapsed bag 92 is put into the same place with the IV spike 90 inserted into the bag 92.

Depending upon the relative quality of the feedwater, the time to collect one liter of solution will vary between three to four minutes. Higher quality feedwater will produce water for injection in less time.

It should be noted that drain tube 42 which is attached to the prefilter and reverse osmosis module 40 is led to the outside of cover 48 so that wastewater generated during operation can be discharged onto the ground. Discharge valve 78 located on drain tube 42 is turned to one of several positions, as previously described in FIG. 5, according to the relative quality of the feedwater.

A trace of the water path through the device aids in understanding the novelty of the invention. When crank handles 30 are turned, rollers (not shown) within peristaltic pump 36 move around in a circular direction, squeezing pump inlet tube 26 against the inner wall of pump 36. The squeezing action draws and forces feedwater through the tubing without any contact of the water with the parts of the pump. Pressures up to 120 psi are generated along with flow rates of up to 1.3 liters per minute.

Pressurized feedwater enters prefilter and reverse osmosis module 40 where it initially passes through a coarse filter spool 62 which removes mud, sand, dirt, leaves, debris and other coarse contaminants that could clog the inlet passages of the reverse osmosis element 70. As shown in FIG. 2, the prefilter and reverse osmosis module 40 is a sealed housing, preferably made of PVC plastic, fiberglass or other plastic known in the art, which contains the two aforementioned components; a coarse filter spool 62 and a reverse osmosis element 70. In this invention they have been designed as two integral elements on the same central core 74 and encapsulated within the same plastic housing of module 40.

Feedwater enters the module 40 at connection 60 and passes through coarse filter spool 62 from the outer surface to the inner core 74. This prefiltered water flows through the inner core 74 to the upstream chamber 68 of reverse osmosis element 70, to the inlet face of reverse osmosis element 70. From there it passes into reverse osmosis element 70 itself, passing between the layers of the reverse osmosis membrane until exiting the outlet face and into the downstream chamber 72.

Reverse osmosis element 70 is a commercially available water purification device which is, in the preferred embodiment, made of a very large area of a double sheet of cellulose or other plastic membrane, sealed along the perimeter, forming an inner chamber between the two layers of membrane. The sheets are attached to a plastic core such that the inner chamber is connected to the inside of the core through small holes in the walls of the core. A double sheet is rolled up around the core forming a spiral. One or more layers of plastic screen material are rolled in with the membranes in order to space the membranes apart and permit the flow of water on both sides of the membranes. Reverse osmosis element 70, used in this invention, measures 12" in length by 4" in diameter. Obviously, other configurations of reverse osmosis elements exist, the most common being a hollow fiber element, which can also be used.

In a reverse osmosis element, such as 70, impure water (the "salt" side) is pressurized and made to flow along the layers of a spirally wound flat chamber of membrane. Water molecules that penetrate the membrane, enter the chamber and spiral in towards the central core 74 of the element 70. Some very small molecules, such as sodium chloride, will also penetrate the membrane. The water thus produced is not, therefore, ultra pure. In this invention, however, the vast majority of the remainder, including contaminants such as dirt, large molecules (mainly organic) and many small molecules, flow along and remain in the upstream passages and are ultimately rejected, going to drain line 42 and thence to the ground. In this regard, rejected water exits the module 40 at fitting 76 into drain tube 42 which passes through discharge valve 78 and thence to the ground. Discharge valve 78 has a variety of positions. The tightest position, as previously discussed, restricts the reject water the most thereby causing more water molecules to pass through the membrane of reverse osmosis element 70 and increases the flow of pure water. As the restriction is lessened, the amount of rejected water going to the drain tube 42 is increased and consequently less pure water is produced. While it might seem that the tightest setting should always be used for maximum conversion into pure water, this may not be the best use of the device. The reason is that, for a given amount of dissolved salts, severe restriction of valve 78, thereby allowing only a small amount of reject water, can cause a condition of saturation of the device and salts would come out of solution. That is, they would precipitate on the surfaces of the membranes of reverse osmosis element 70 and cause a condition called "fouling". Fouling leads to the shut down or drastic reduction of the performance of the reverse osmosis membrane. Obviously, the higher the feedwater quality, the less dissolved salts it will contain and the less can be the reject water volume or flow rate. The tightest position of the valve will produce approximately 300 ml per minute of pure water from drinking water used as feedwater.

Once the pure water exits module 40, it flows to the top of the carbon column 44. Entering the carbon column 44 at inlet 80 it flows down through the column of carbon 96 past trap filter 98 and out outlet 82. Containing activated carbon 96, carbon column 44 removes organic molecules, halogens and certain other molecules by adsorption. Flow direction is downward. Flow continues through connecting tubing to the bottom of ion exchange column 46 and enters ion exchange column 46 at inlet 100. Ion exchange column 46 is filled with pure mixed bed ion exchange resin 103. The outlet section of ion exchange column 46 is typically packed with approximately of 2" of packed glass or polypropylene filter 105 which serves as a trap filter preventing pieces of ion exchange resin from passing downstream. The ion exchange resin 103 removes most of the ionizable substances, silica and carbon dioxide. Flow in ion exchange column 46, when in place in device 10, is upward.

At this point, ultra pure water exits from outlet 102 at the top of ion exchange column 46 and flows through transfer tube 84 under pump 36 and connects with sterilizing filter 38 at inlet 86. The sterilizing filter 38 in this design is known in the art and, for example, may be of a type manufactured by the Pall Corporation (Glen Cove, N.Y.). It is a commercially available presterilized, capsule-type filter, incorporating a pleated filter element welded to its own plastic housing. The element is a microporous nylon microfilter rated at either 0.1 or 0.2 microns. The membrane of filter 38 has a positive charge. Due to the very small pore size rating, water passing through it is sterilized. The positive charge serves to remove pyrogens and any organics that may still be in the ultrapure water. Water exiting the sterilizing filter 38 and emerging through IV spike 90 is sterile, non-pyrogenic intravenous solution and water for injection.

While the present invention has been disclosed in connection with the preferred embodiment thereof, it should be understood that there may be other embodiments which fall within the spirit and scope of the invention as defined by the following claims.

What is claimed is:

1. A portable intravenous solutions method comprising the steps of:
   A. constructing a frame;
   B. providing a pump means for pumping liquid to be filtered and attaching said pump means to said frame;
   C. constructing a filter means and connecting said filter means to said pump means so that said liquid discharged from said pump means is forced through said filter means;
   D. providing a final stage of said filter means from which sterile, non-pyrogenic intravenous solutions and water for injection is discharged;
   E. providing a hollow box means, in said frame, with a base and a top, with a rigid center section to which said pump means and said filter means are attached;
   F. constructing a handle means, which is part of said rigid center section, across said top of said hollow box means for use as a handle in carrying;
   G. attaching removably attachable top and sides to said base so that easy access to the interior of said box means is attained once said apparatus is placed in operation; and
   H. attaching a collapsible cranking means to said box means for manual operation of said pump means.

2. The portable intravenous solutions method of claim 1 wherein providing a pump means comprises the steps of:
   A. connecting a shaft to said cranking means;
   B. attaching a roller means to said shaft;
   C. providing an inlet end of a tube, for transmission of liquid to said filter means, and passing said tube inside said roller means so that when said cranking means turns said shaft, said roller means rhythmically compresses said tube against the housing of said pump means causing a suction at said inlet end of said tube; and
   D. connecting an outlet end of said tube to said filter means.

3. The portable intravenous solutions method of claim 2 further comprising the step of providing a reservoir tank within said box means, for holding a quantity of liquid, constructed with an outlet port to which said inlet end of said tube may be attached.

4. The portable intravenous solutions method of claim 3 wherein constructing a filter means comprises the steps of:
   A. providing a combination prefilter and reverse osmosis module and placing said combination in a sealed container wherein said prefilter removes coarse contaminants and said reverse osmosis module passes contaminated liquid to a drain and purified liquid to an exit;
   B. connecting a carbon column means to said exit on said reverse osmosis module so that purified liquid flows therethrough and organic molecules and halogens are removed and purified liquid passes to an exit; and
   C. attaching an ion exchange column means to said carbon column means exit so that purified liquid flows therethrough and ionizable substances are removed and ultrapure water passes to an exit.

5. The portable intravenous solutions method of claim 4 wherein providing a final stage comprises the steps of:
   A. connecting a sterilizing filter means to said exit on said ion exchange means that removes pyrogens and any remaining organics so that sterile, non-pyrogenic water for injection is passed to an exit; and
   B. attaching an intravenous spike means to said sterilizing filter exit so that said sterile, non-pyrogenic intravenous solutions and water for injection may be pumped through said spike means into dry, pre-packaged intravenous bags containing measured amounts of medicines for reconstitution.

6. The portable intravenous solutions method of claim 5 further comprising the step of providing a reject valve means for increasing pressure within said filter means by restricting the flow of said contaminated liquid to said drain.

7. The portable intravenous solutions method of claim 6 wherein said step of providing a reject valve means further comprises the step of providing a multiposition restriction means so that when liquid quality at said inlet is high, reject flow rate can be reduced to a minimum without undue fouling of said filter means and when liquid quality at said inlet is low, reject flow rate can be increased so as to reduce fouling of said flter means.

8. The portable intravenous solutions method of claim 7 wherein said method produces 300 ml per minute of sterile, non-pyrogenic intravenous solutions and water for injection from drinking water and 20 to 40 liters of said sterile, non-pyrogenic intravenous solutions and water for injection from all sources of water prior to depletion of said filter means.

9. The portable intravenous solutions method of claim 2 further comprising the step of providing a remote suction tube means, one end of which is conformed to connect with said inlet end of said tube and one end of which may be placed within a remote body of liquid for suction thereof.

10. A portable intravenous solutions method comprising the steps of:
    A. constructing a frame;

B. providing a pump means for pumping liquid to be filtered and attaching said pump means to said frame;

C. constructing a filter means and connecting said filter means to said pump means so that said liquid discharged from said pump means is forced through said filter means;

D. providing a final stage of said filter means from which sterile water for injection is discharged;

E. the step of constructing a frame further comprising the step of providing a hollow box means with a base and a top, with a rigid center section to which said pump means and said filter means are attached;

F. Constructing a handle means, which is part of said rigid center section, across said top of said hollow box means for use as a handle in carrying;

G. attaching removably attachable top and sides to said base so that easy access to the interior of said box means is attained once said apparatus is placed in operation;

H. attaching a collapsible cranking means to said box means for manual operation of said pump means;

I. the step of providing a pump means further comprising the step of connecting a shaft to said cranking means;

J. attaching a roller means to said shaft;

K. providing an inlet end of a tube, for transmission of liquid to said filter means, and passing said tube inside said roller means so that when said cranking means turns said shaft, said roller means rhythmically compresses said tube against the housing of said pump means causing a suction at said inlet end of said tube;

L. connecting an outlet end of said tube to said filter means;

M. providing a reservoir tank within said box means, for holding a quantity of liquid, constructed with an outlet port to which said inlet end of said tube may be attached;

N. providing a combination prefilter and reverse osmosis module and placing said combination in a sealed container wherein said prefilter removes coarse contaminants and said reverse osmosis module passes contaminated liquid to a drain and purified liquid to an exit;

O. connecting a carbon column means to said exit on said reverse osmosis module so that purified liquid flows therethrough and organic molecules and halogens are removed and purified liquid passes to an exit;

P. attaching an ion exchange column means to said carbon column means exit so that purified liquid flows therethrough and ionizable substances are removed and ultrapure water passes to an exit;

Q. connecting a sterilizing filter means to said exit on said ion exchange means that removes pyrogens and any remaining organics so that sterile, non-pyrogenic water for injection is passed to an exit;

R. attaching an intravenous spike means to said sterilizing filter exit so that said sterile, non-pyrogenic water for injection may be pumped through said spike means into dry, prepackaged intravenous bags containing measured amounts of medicines for reconstitution; and S. providing a reject valve means for increasing pressure within said filter means by restricting the flow of said contaminated liquid to said drain.

11. The portable intravenous solutions method of claim 10 further comprising the step of providing a remote suction tube means, one end of which is conformed to connect with said inlet end of said tube and one end of which may be placed within a large remote body of liquid for suction thereof.

12. The portable intravenous solutions method of claim 11 wherein the step of providing said reject valve means further comprises the step of providing of a multi-position restriction means so that when liquid quality at said inlet is high, reject flow rate can be reduced to a minimum without undue fouling of said filter means and when liquid quality at said inlet is low, reject flow rate can be increased so as to reduce fouling of said filter means.

13. The portable intravenous solutions method of claim 12 wherein said method produces 300 ml per minute of sterile, non-pyrogenic intravenous solutions and water for injection from drinking water and 20 to 40 liters of said sterile, non-pyrogenic intravenous solutions and water for injection from all sources of water prior to depletion of said filter means.

14. A portable intravenous solutions apparatus comprising;

A. a frame

B. a pump means mounted on said frame for pumping liquid to be filtered;

C. a filter means connected to said pump means so that said liquid discharged from said pump means is forced through said filter means;

D. a final stage of said filter means from which sterile water for injection is discharged;

E. a hollow box means, of said frame, with a base and top, with a rigid center section to which said pump means and said filter means are attached;

F. a handle means, which is part of said rigid center section, across said top of said hollow box means for use as a handle in carrying;

G. removably attachable top and sides attached to said base so that easy access to the interior of said box means is attained once said apparatus is placed in operation; and H. a collapsible cranking means attached to said box means for manual operation of said pump means.

15. The portable intravenous solutions apparatus of claim 14 wherein said pump means comprises:

A. a shaft connected to said cranking means;

B. a roller means attached to said shaft;

C. an inlet end of a tube, for transmission of liquid to said filter means, which passes inside said roller means so that when said cranking means turns said shaft, said roller means rhythmically compresses said tube against the housing of said pump means causing a suction at said inlet end of said tube; and D. an outlet end of said tube connected to said filter means.

16. The portable intravenous solutions apparatus of claim 15 further comprising a reservoir tank within said box means, for holding a quantity of liquid, with an outlet port to which said inlet end of said tube may be attached.

17. The portable intravenous solutions apparatus of claim 16 wherein said filter means comprises:

A. a combination prefilter and reverse osmosis module in a sealed container wherein said prefilter removes coarse contaminants and said reverse osmosis module passes contaminated liquid to a drain and purified liquid to an exit;

B. a carbon column means connected to said exit on said reverse osmosis module so that purified liquid flows therethrough and organic molecules and halogens are removed and purified liquid passes to an exit; and C. an ion exchange column means attached to said carbon column means exit so that purified liquid flows therethrough and ionizable substances are removed and ultrapure water passes to an exit.

18. The portable intravenous solutions apparatus of claim 17 wherein said final stage comprises:

A. a sterilizing filter means connected to said exit on said ion exchange means that removes pyrogens and any remaining organics so that sterile, non-pyrogenic intravenous solutions and water for injection are passed to an exit; and B. an intravenous spike means attached to said sterilizing filter exit so that said sterile, non-pyrogenic intravenous solutions and water for injection may be pumped through said spike means into dry, prepackaged intravenous bags containing measured amounts of medicines for reconstitution.

19. The portable intravenous solutions apparatus of claim 18 further comprising a reject valve means for increasing pressure within said filter means by restricting the flow of said contaminated liquid to said drain.

20. The portable intravenous solutions apparatus of claim 19 wherein said reject valve means further comprises a multi-position restriction means so that when liquid quality at said inlet is high, reject flow rate can be reduced to a minimum without undue fouling of said filter means and when liquid quality at said inlet is low, reject flow rate can be increased so as to reduce fouling of said filter means.

21. The portable intravenous solutions apparatus of claim 20 wherein said apparatus produces 300 ml per minute of sterile, non-pyrogenic intravenous solutions and water for injection from drinking water and 20 to 40 liters of said sterile, non-pyrogenic intravenous solutions and water for injection from all sources of water prior to depletion of said filter means.

22. The portable intravenous solutions apparatus of claim 15 further comprising a remote suction tube means, one end of which is conformed to connect with said inlet end of said tube and one end of which may be placed within a remote body of liquid for suction thereof.

23. A portable intravenous solutions apparatus comprising:

A. a frame:

B. a pump means mounted on said frame for pumping liquid to be filtered;

C. a filter means connected to said pump means so that said liquid discharged from said pump means is forced through said filter means;

D. a final stage of said filter means from which sterile water for injection is discharged;

E. said frame further comprising a hollow box means with a base and a top, with a rigid center section to which said pump means and said filter means are attached;

F. a handle means, which is part of said rigid center section, across said top of said hollow box means for use as a handle in carrying;

G. removably attachable sides attached to said base so that easy access to the interior of said box means is attained once said apparatus is placed in operation;

H. a collapsible cranking means attached to said box means for manual operation of said pump means;

I. said pump means further comprising a shaft connected to said cranking means;

J. a roller means attached to said shaft;

K. an inlet end of a tube, for transmission of liquid to said filter means, which passes inside said roller means so that when said cranking means turns said shaft, said roller means rythmically compresses said tube against the housing of said pump means causing a suction at said inlet end of said tube;

L. an outlet end of said tube connected to said filter means;

M. a reservoir tank within said box means, for holding a quantity of liquid, with an outlet port to which said inlet end of said tube may be attached;

N. said filter means further comprising a combination prefilter and reverse osmosis module in a sealed container wherein said prefilter removes coarse contaminants and said reverse osmosis module passes contaminated liquid to a drain and purified liquid to an exit;

O. a carbon column means connected to said exit on said reverse osmosis module so that purified liquid flows therethrough and organic molecules and halogens are removed and purified liquid passes to an exit;

P. an ion exchange column means attached to said carbon column means exit so that purified liquid flows therethrough and ionizable substances are removed and ultrapure water passes to an exit;

Q. said final stage further comprising a sterilizing filter means connected to said exit on said ion exchange means that removes pyrogens and any remaining organics so that sterile, non-pyrogenic water for injection is passed to an exit;

R. an intravenous spike means attached to said sterilizing filter exit so that said sterile, non-pyrogenic water for injection may be pumped through said spike means into dry, prepackaged intravenous bags containing measured amounts of medicines for reconstitution; and S. a reject valve means for increasing pressure within said filter means by restricting the flow of said contaminated liquid to said drain.

24. The portable intravenous solutions apparatus of claim 23 further comprising a remote suction tube means, one end of which is conformed to connect with said inlet end of said tube and one end of which may be placed within a remote body of liquid for suction thereof.

25. The portable intravenous solutions apparatus of claim 24 wherein said reject valve means further comprises a multi-position restriction means so that when liquid quality at said inlet is high, reject flow rate can be reduced to a minimum without undue fouling of said filter means and when liquid quality at said inlet is low, reject flow rate can be increased so as to reduce fouling of said filter means.

26. The portable intravenous solutions apparatus of claim 25 wherein said apparatus produces 300 ml per minute of sterile, non-pyrogenic intravenous solutions and water for injection from drinking water and 20 to 40 liters of said sterile, non-pyrogenic intravenous solutions and water for injection from all sources of water prior to depletion of said filter means.

* * * * *